United States Patent [19]
Olsen

[11] Patent Number: 5,951,949
[45] Date of Patent: Sep. 14, 1999

[54] HEAT EXCHANGER FOR MEDICAL APPLICATIONS

[75] Inventor: Robert W. Olsen, Plymouth, Minn.

[73] Assignee: Avecor Cardiovascular Inc., Brooklyn Park, Minn.

[21] Appl. No.: 08/993,917

[22] Filed: Dec. 18, 1997

Related U.S. Application Data

[63] Continuation-in-part of application No. 08/855,675, May 14, 1997.

[51] Int. Cl.[6] .............................. A61M 1/14; A61M 1/34; A61M 1/36
[52] U.S. Cl. ................................................ 422/46
[58] Field of Search .................. 422/44–46; 165/48, 165/149, 46, 173, 172, 174, 179, 157, 158

[56] References Cited

U.S. PATENT DOCUMENTS

| | | | |
|---|---|---|---|
| D. 281,717 | 12/1985 | Pavlov et al. . | |
| 4,585,056 | 4/1986 | Oscarsson . | |
| 4,653,577 | 3/1987 | Noda | 165/71 |
| 4,735,775 | 4/1988 | Leonard et al. . | |
| 4,883,455 | 11/1989 | Leonard | 604/4 |
| 5,167,921 | 12/1992 | Gordon | 422/45 |
| 5,255,734 | 10/1993 | Leonard et al. | 165/96 |
| 5,269,749 | 12/1993 | Koturov . | |
| 5,411,705 | 5/1995 | Thor et al. . | |
| 5,421,405 | 6/1995 | Goodin et al. . | |
| 5,429,184 | 7/1995 | Bach et al. | 165/149 |
| 5,609,571 | 3/1997 | Buckberg et al. . | |
| 5,651,765 | 7/1997 | Haworth et al. . | |
| 5,706,889 | 1/1998 | Bach et al. | 165/172 |
| 5,766,480 | 6/1998 | Cosentino et al. | 210/644 |

*Primary Examiner*—John G. Weiss
*Assistant Examiner*—Ki Yong O

[57] ABSTRACT

A heat exchanger for medical applications is disclosed. The heat exchanger is characterized in that it is configured to provide a high heat transfer efficiency while minimizing the possibility of formation gaseous emboli and maximizing the ability to entrap and remove any such emboli which form or are introduced into the device. The heat exchanger has a corrugated tubular core which is configured to minimize the chances of entrapping air during the potting process.

8 Claims, 7 Drawing Sheets

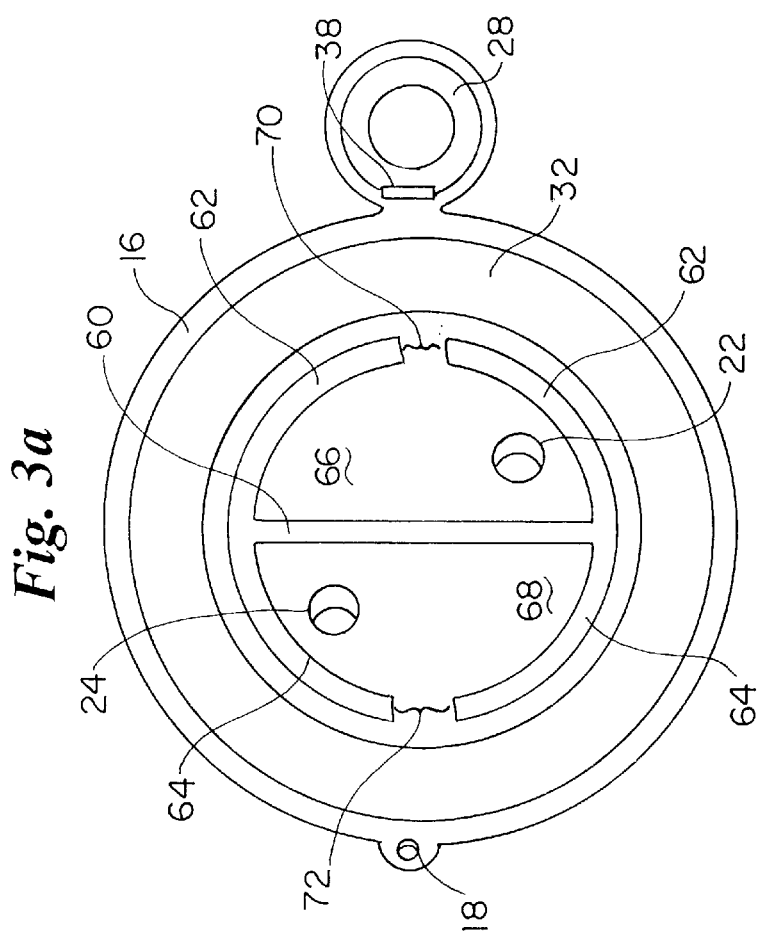
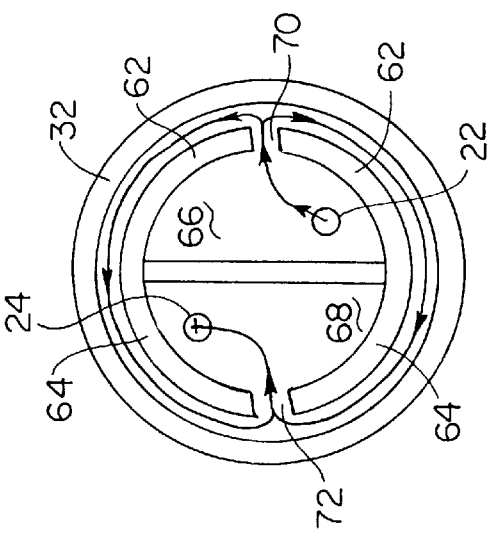

HEAT EXCHANGER FOR MEDICAL APPLICATIONS

This is a continuation-in-part of co-pending U.S. patent application Ser. No. 08/855,675 filed May 14, 1997.

FIELD OF THE INVENTION

The present invention is in the field of heat exchangers adapted for use in medical applications. More particularly, the present invention relates to a heat exchanger having a corrugated tubular core which is shaped to improve the reliability of the manufacturing process.

BACKGROUND

Many surgical procedures, especially those involving cardiac surgery, require that blood be shunted around the surgical site by means of an extracorporeal circuit. For example, during open heart surgery, the beating of the heart must often be temporarily stopped. Of course, while the heart is stopped, it is still necessary to prevent ischemia to the heart muscle which may result in permanent damage, while also providing circulation of blood to the brain and other vital organs. In connection with the need to oxygenate and circulate the blood, it is often necessary to maintain the blood at a particular temperature or to raise or lower the temperature of the blood.

The heart can be protected during open heart surgery using a method known as cold cardioplegia. In that method, a chilled cardioplegia solution is provided to the heart. The cardioplegia solution typically comprises a crystalloid chemical solution which includes potassium, either alone or in combination with other additives. The solution may also be combined with blood obtained from the patient or other suitable donor. Thus, as used herein, the term "cardioplegia solution" is intended to encompass fluids used in an extracorporeal circuit which comprise crystalloid solution, blood, or any combination of crystalloid solution and blood. The use of chilled cardioplegia solution is known to be effective in maintaining the heart in an arrested state, while simultaneously maintaining an appropriate level of oxygen to the heart muscle. Thus, a means must be provided for chilling the cardioplegia solution as well as for returning the solution to physiological temperature.

More recently, a new procedure, referred to as warm continuous blood cardioplegia, has attracted some interest among cardiac surgeons. In this procedure, the cardioplegia solution is not cooled. That notwithstanding, it may still be desirable to maintain the ability to control the temperature of cardioplegia solution in the extracorporeal circuit.

In either method, temperature of the cardioplegia solution can be maintained or controlled using a heat exchanger. It is desirable that the heat exchanger be designed to allow highly efficient heat transfer without causing a substantial pressure drop. It is known in the art to use heat exchangers having a corrugated metal core or bellows, for example, a corrugated stainless steel core, as the heat transfer barrier. The use of such cores is desirable because the metal offers excellent heat transfer characteristics while acting as a strong barrier between the fluids among which heat is being exchanged. The corrugations serve to increase the total surface area available for heat transfer while still allowing the device to remain relatively compact. Although concurrent and cross-current designs are known in the art, preferred heat exchangers have counter-current designs. In these systems, a first fluid flows along one side of the barrier in one direction and a second fluid flows along the other side of the barrier in a parallel, but opposite, direction.

In the case of a heat exchanger being used to control the temperature of cardioplegia solution, the solution can be chilled or heated as it flows along one side of the heat exchange barrier by water which is flowed in the opposite direction along the other side of the barrier. It is desirable that the side of the heat exchange device which accommodates the cardioplegia solution be designed to minimize the pressure drop between the device inlet and the device outlet. Additionally, the solution side of the heat exchanger is preferably designed to: a) minimize the formation of air bubbles, b) maximize the ability to entrap any air bubbles which may be present, c) eliminate stagnant zones, and d) minimize damage to blood cells that may be present in the solution.

In contrast, since water is typically used as the medium with which the cardioplegia solution exchanges heat, and since the heat exchange water will not be subjected to the limitations of operating within a complex biological circuit, many of the considerations applicable to the cardioplegia solution side of the barrier do not apply on the water side of the barrier.

In the discussion above, heat exchangers have been described for use in systems adapted for handling cardioplegia solution. It should be understood, however, that similar conditions and considerations are applied when using heat exchangers in other medical apparatus. For example, U.S. Pat. No. 5,421,405 (Goodin et al.), the teachings of which are incorporated herein by reference, describes a heat exchanger for use in blood oxygenation systems.

When heat exchangers having tubular corrugated metal cores are constructed, each end of the metal core is commonly embedded in a potting compound to form a leak proof seal. This prevents the cardioplegia solution from mixing with the water. During construction of these devices the ends of the corrugated core or bellows are usually potted one end at a time. With the axis of the core being vertically oriented the end to be potted is placed at the bottom. Since each side wall of the corrugations of the core including the end corrugation are normal to the axis of the core, when the end of the core is placed in the potting compound there is an opportunity for air bubbles to be trapped between the end corrugation and the potting compound. This is undesirable since it compromises the seal and requires that the unit be discarded.

Despite the well developed art of medical heat exchanger design, a need still exists for improved medical heat exchangers. In particular, a need exists for a heat exchanger with a corrugated core that is shaped so that the integrity of the seal is not compromised when the unit is potted. This improves the reliability of the manufacturing process, enhances safety and reduces waste.

SUMMARY OF THE INVENTION

The present invention relates to an improved heat exchanger for use in medical applications, and more particularly, to a heat exchanger having an improved corrugated tubular core.

The heat exchanger comprises a housing formed of a biocompatible material and having a first end and a second end. The heat exchanger further includes a heat exchanger core which comprises a tube having a first end and a second end and a longitudinal axis. The core has a plurality of circumferential corrugations including first and second end corrugations adjacent the first and second ends of the core, respectively. The corrugations define a plurality of exterior flow channels and interior flow channels. The first end corrugation has a first side surface adjacent the first end of the core and the second end corrugation has a first side surface adjacent the second end of the core. A first sealing member is disposed between the first end of the housing and the first side surface of the first end corrugation. A second sealing member is disposed between the second end of the housing and the first side surface of the second end corrugation. One or both of the first side surfaces of the first and second end corrugations are positioned at an acute angle relative to a plane normal to the axis of the core. The housing, core and first and second sealing members together define a biological fluid flow path across the exterior flow channels in communication with a biological fluid inlet and a biological fluid outlet. The core, housing and first and second sealing members further define a heat exchanging medium flow path across the interior flow channels in communication with a heat exchanging medium inlet and a heat exchanging medium outlet. The biological fluid flow path and the heat exchange medium flow path are isolated from one another.

In one embodiment, the acute angle at which one or both of the first side surfaces of the first and second end corrugations are positioned relative to a plane normal to the axis of the core is between about 3° and 15°. In a further embodiment, the heat exchanger core is substantially cylindrical. In another embodiment, each of the corrugations other than the first and second end corrugations have substantially opposing side surfaces which are positioned substantially parallel to a plane normal to the longitudinal axis of the core.

Each of these features will be described in greater detail below, with reference to the accompanying Figures.

BRIEF DESCRIPTION OF THE DRAWINGS

FIG. 3a is a schematic representation of one embodiment of a lower housing portion of the heat exchanger of the present invention.

FIG. 3b is a schematic representation of a heat exchanging medium flow path through one embodiment of the heat exchanger of the present invention.

FIG. 6a is an enlarged view of a detail of FIG. 6.

DETAILED DESCRIPTION OF THE INVENTION

Figure 1:
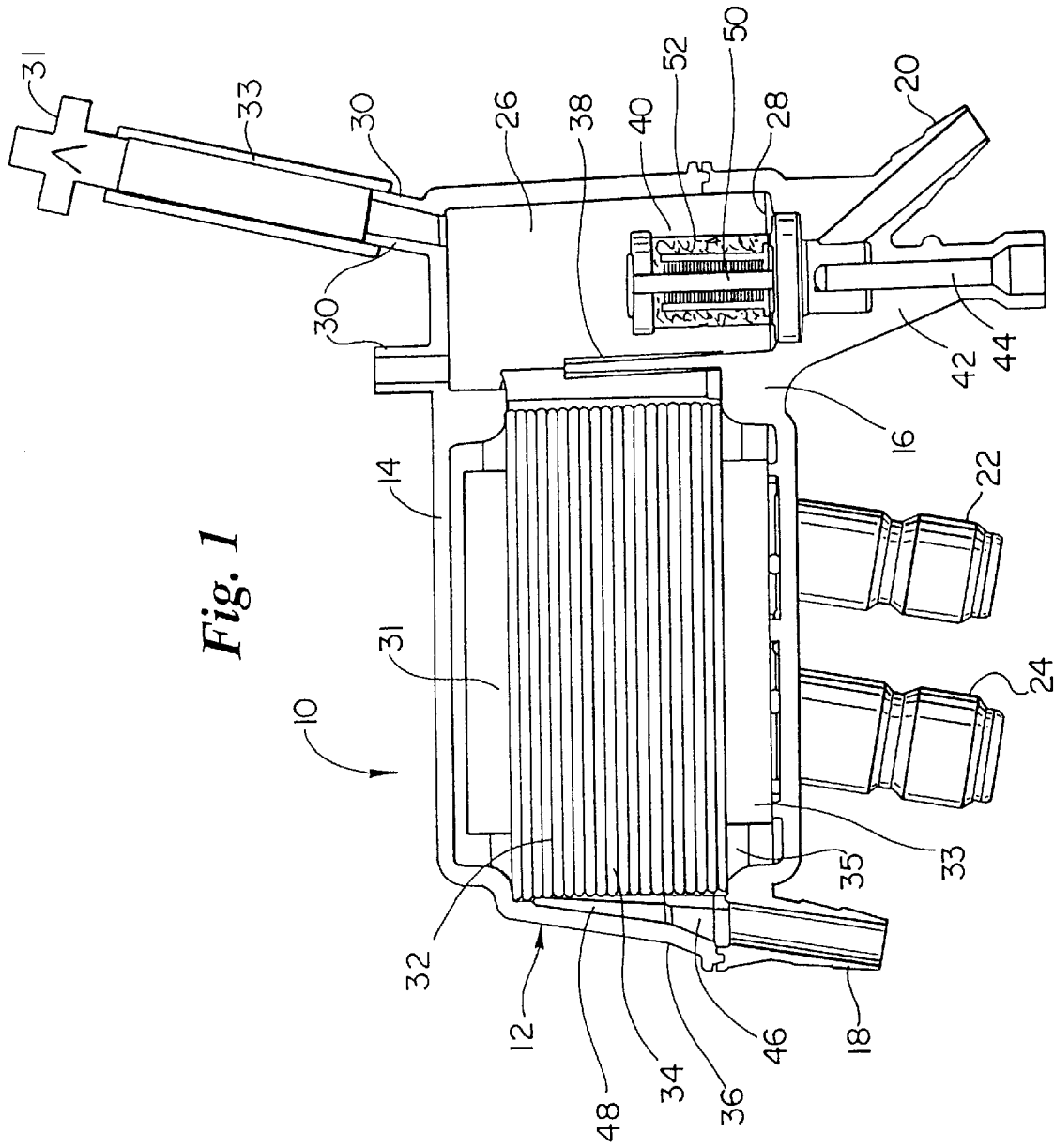
FIG. 1 is a schematic elevation of one embodiment of a heat exchanger of the present invention.

One embodiment of the present invention is presented in FIG. 1. In FIG. 1, a heat exchanger 10 comprises a housing 12 having upper 14 and lower 16 portions. The lower portion 16 of the housing includes a biological fluid inlet 18, a biological fluid outlet 20, a heat exchanging medium inlet 22, and a heat exchanging medium outlet 24. The housing further defines a gas entrapment chamber 26 having a floor 28. The gas entrapment chamber is further provided with at least one vent 30 to which a remote pressure relief valve 31 may be attached via tubing 33. As will be discussed in detail below, the use of two luer-lock vents is preferred. The heat exchanger 10 further includes a heat exchanger core 32. The core 32 comprises a tube into which have been formed a plurality of substantially parallel, circumferential corrugations 34 which define exterior and interior flow channels. The core may be substantially cylindrical as shown in the drawing figures or may have other non-circular cross-sectional configurations such as that of an oval or a rounded square. The core further includes cuffs 31 and 33 at its respective ends. A potting compound (not shown) is used to fill the housing in the regions of the cuffs 31 and 33 in a manner which will be discussed in more detail with respect to FIGS. 6–8. As best seen in FIG. 3a and 3b, small raised portions or shoulders 35 are provided on lower portion 16. The corrugation at the end of the core adjacent to cuff 33 rests against standoffs 35 to space the corrugation from the surface of the lower portion. Similar standoffs (not shown) on upper portion 14 space the corrugation adjacent cuff 31 from the surface of upper portion 14.

The biological fluid inlet 18 is in fluid communication with the biological fluid outlet 20 via a biological fluid flow path, and the heat exchanging medium inlet 22 is in fluid communication with the heat exchanging medium outlet 24 via a heat exchanging medium flow path. The only communication between the biological fluid flow path and the heat exchanging medium flow path is by the transfer of heat across the heat exchanger core 32 which acts as an impermeable barrier to separate the flow paths.

The biological fluid flow path begins at the biological fluid inlet 18. Fluid entering the inlet enters a variable pitch manifold 36 and is directed into the exterior flow channels of the core 32. After passing through the exterior flow channels, the fluid encounters a biological fluid flow diverter wall 38 positioned at the entrance of the gas entrapment chamber. The biological fluid flow diverter wall 38 directs the fluid in an upward direction until it flows over the top of the biological fluid flow diverter wall. The fluid then flows downward through a filter 40 and through the biological fluid outlet 20. A temperature sensing port 42, within which is mounted a metallic temperature sensor adapter 44, may be provided to allow the temperature of the biological fluid exiting the device to be monitored. The temperature of the biological fluid exiting the device can be controlled by controlling the temperature and/or flowrate of the heat exchanging medium flowing in the heat exchanging medium flow path. This aspect of the invention will be described in detail below.

One important aspect of the present invention is that it is configured to provide efficient heat transfer, while at the same time seeking to entrap any gaseous emboli that form in or are introduced into the device. Additionally, the device is configured in a manner such that, during priming with the biological fluid, it is possible to remove virtually all air that was resident in the device prior to priming.

In order to achieve a high level of prevention and entrapment of gaseous emboli, various inventive aspects have been included in the device. Before discussing these inventive aspects, however, a clear understanding of the origin of gaseous emboli is necessary. Initially, prior to its use, the device naturally contains a volume of air or other gas that occupies the biological fluid flow path and the heat exchanging medium flow path. The volume of fluid (biological or heat exchanging) that is necessary to displace the gas in each flow path is referred to herein as the priming volume. There is a priming volume for both the biological fluid flow path and the heat exchanging medium flow path, however, the latter is unimportant, since it will not be subject to the undesirable property of introducing gaseous emboli into a patient. It is very important, however, to minimize the possibility of gaseous emboli being introduced to the patient via the biological fluid flow path.

As the device is put into use, biological fluid entering the biological fluid flow path displaces the gasses previously present. It is desirable that the device be configured to allow the gas being displaced to exit the device rather than becoming entrapped within the device. Likewise, the possibility exists that, once put into service, problems in the extracorporeal flow circuit can result in gaseous emboli forming within or being introduced into the device. Thus, it is very desirable that the device be configured to entrap and allow safe removal of such emboli with a minimum of inconvenience to the operator.

One inventive aspect of the device relates to the priming volume of the biological fluid flow path. In the present invention, the device has been configured such that at least about 40% of the biological fluid flow path priming volume occupies the gas entrapment chamber rather than the exterior flow channels. For example, in one preferred embodiment, the priming volume of the inlet manifold and the exterior flow channels is about 10 cc, whereas the priming volume of the gas entrapment chamber is approximately 35 cc. Because the priming volume within the inlet manifold and flow channels is low relative to that of the gas entrapment chamber, a large percentage of the priming volume is available to entrap gas before any gaseous emboli are passed to the patient.

In addition, the device has been configured such that, when the biological fluid inlet is positioned to allow biological fluid to enter the device vertically upward, (a preferred configuration), the core is tilted upward toward the outlet at an angle of about 5° to about 20° relative to horizontal. As such, fluid traveling along the biological fluid flow path through the exterior channels of the heat exchanger core is caused to travel upward toward the outlet at an angle of about 5° to about 20°. In one preferred embodiment, the core is tilted about 10° relative to the horizontal. By tilting the heat exchanger core 32, gasses present in the flow channels are caused to rise both as the device is primed with fluid and during operation, rather than remaining in the channels and forming emboli. The gas then collects in the gas entrapment chamber from which it may be removed.

It should be noted, however, that the relationship between the orientation of the inlet and the exterior flow channels need not be limited to the embodiment described above. Rather, one aspect of the invention is intended to encompass a method of use of the device when it is oriented in a manner such that the exterior flow channels are maintained at an upward angle along the flow path. Thus, regardless of the inlet configuration, the device may be oriented such that biological fluid in the biological fluid flow path is caused to travel upward toward the outlet at an angle of about 5° to about 20°, preferably about 10° upward, relative to horizontal.

In a related embodiment, the heat exchanging medium inlet 22 and outlet 24 are tilted at an angle corresponding to the tilt of the heat exchanger core, so that when the device is mounted with the core at its tilted configuration, the inlet 22 and outlet 24 extend perpendicularly downward from the device. This configuration minimizes strain on the inlet 22 and outlet 24 when they are attached to tubing which supplies and receives the heat exchanging medium as it flows through the device.

Additionally, the device can be provided with a variable pitch manifold 36 through which a biological fluid enters the exterior flow channels. The purpose of the variable pitch manifold 36 is to diffuse, (i.e., slow) biological fluid velocity and to distribute the biological fluid substantially uniformly among the several exterior flow channels on the heat exchanger core. As can be seen in FIG. 1, the manifold 36 has a high pitch section 46 and a low pitch section 48. In one embodiment, the high pitch section 46 of the variable pitch manifold 36 is angled toward the heat exchanger core at an angle of about 20° to about 30°, and most preferably at an angle of about 25.1°. Likewise, the low pitch section 48 of the variable pitch manifold 36 is angled toward the heat exchanger core at an angle of about 5° to about 15°, and most preferably at an angle of about 9.7°. It is noted that each of these angles is given relative to the side of the heat exchanger core 32.

The variable pitch manifold 36 distributes the biological fluid entering the flow channels in a substantially uniform manner. Such uniformity is achieved as follows. Fluid entering the manifold typically has a relatively high velocity because it is entering through a relatively small diameter inlet (approx. 0.635 cm). As the fluid enters the manifold, a portion of the incoming fluid is caused to make a sharp turn into the initial corrugations 34 of the heat exchanger core 32. To help the flow negotiate the sudden turn, the high pitch section of the manifold deflects the fluid toward the corrugations of the heat exchanger core. The manifold also includes a sudden widening to further enhance the velocity reduction and to provide a larger area for the fluid to enter the flow channels. Additionally, the low pitch section 48 of the manifold tends to contain fluid having a lower flow velocity due to the diffusing effect of the forward section of the manifold. The combination of the variable pitch and the widened flow path causes the biological fluid to be substantially uniformly distributed among the flow channels. By providing a manifold which enhances uniform fluid distribution among the various flow channels, it is possible to provide maximum heat exchange effectiveness.

The biological fluid flow diverter wall 38 provides an effective means for diverting any gaseous emboli which may have become entrained in the biological fluid flow path. Specifically, as the biological fluid exits an exterior flow channel along the flow path to the gas entrapment chamber 26, it encounters the biological fluid flow diverter wall 38 which directs the fluid flow upward. Upon reaching the top of the biological fluid flow diverter wall, the fluid turns downward to access the filter 40 and the biological fluid outlet 20. This redirection of the fluid flow assists in shedding any gaseous emboli that may have become entrained in the fluid. The emboli rise in the gas entrapment chamber and can be removed through a vent 30, preferably threaded to allow mating with a luer-lock. Additionally, the biological fluid flow diverter wall 38 acts as a barrier between the flow channels and the filter 40. In so doing, any emboli-containing fluid is prevented from flowing directly to the filter where there would be a possibility of gaseous emboli lodging at the filter or passing through the filter into the biological fluid outlet.

As noted above, a pressure relief valve 31 can be connected to one of the vents 30 via a length of medical grade tubing 33. The pressure relief valve can relieve excessive pressures present in the device, thus preventing damage to the device or injury to the patient, and also provides a means for releasing entrapped gas from the system. The pressure at which release occurs will depend upon selection of the particular valve. In the preferred embodiment of two luer-lock threaded vents 30, the pressure relief valve can be connected to one vent and a pressure monitoring appliance (not shown) can be connected to the other vent.

The use of at least one vent mounted to the top of the device allows a novel system for removing gas that becomes entrapped in the device, either during priming or use. By simply clamping or otherwise obstructing the biological fluid outlet, any gas resident in the gas entrapment chamber 26, will be displaced by biological fluid gathering in the gas entrapment chamber and forced out of the device through the pressure relief valve. This allows a simple and very quick means for removing gas from the extracorporeal circuit without the need to stop or reduce fluid circulation or to perform complicated fluid rerouting. As such, it is particularly well-suited for an emergency situation in which, for example, a large bolus of air enters the device. In such a case, the operator would simply clamp off the line leading from the biological fluid outlet and allow the biological fluid pump to continue functioning. The air bolus would enter the gas entrapment chamber and then would be forced out of the device, through the pressure relief valve, by biological fluid entering the device behind the bolus. Once the air exits the circuit, the outlet line would be unclamped, and normal operation of the circuit would be allowed to continue.

As noted above, in the preferred embodiment, two vents 30 are provided. As can be seen in FIG. 1, one vent 30 is positioned adjacent to the outer portion of the gas entrapment chamber 26, and a second vent 30 is positioned more toward the heat exchanger core 32. When gas is vented through the outermost vent, it is possible to remove substantially all gas from the gas entrapment chamber. However, if gas is vented through the inboard vent, it is possible to remove only about 90% of the gas from the chamber. This is a result of the inboard vent being positioned slightly lower than the outboard vent when the device is maintained in a manner at which the heat exchanger core is tipped from horizontal. It is noted, however, that 90% gas removal from the gas entrapment chamber still provides satisfactory removal from the device because the small amount of remaining gas is out of the bulk biological fluid flow path and would not be passed to the patient.

Figure 2:
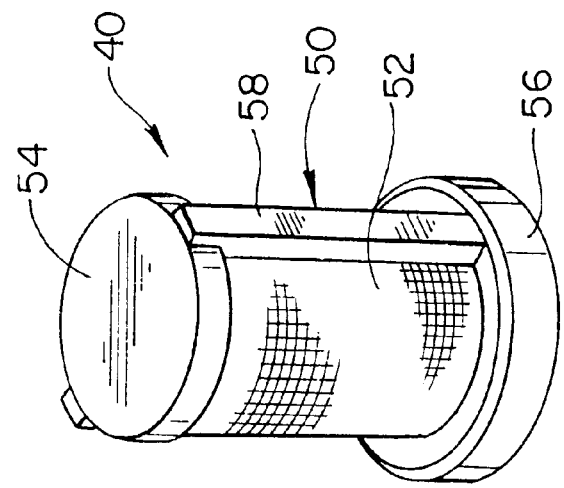
FIG. 2 is a representation of a filter for use with the heat exchanger of the present invention.

The filter 40 is characterized in that it comprises a framework 50 and a filter screen 52. As can be seen in greater detail in FIG. 2, the framework 50 includes a cap 54, supported above a skirt 56 by at least two vertical struts 58. The screen 52 is supported by the framework. In one preferred embodiment of the heat exchange device 10, the skirt 56 of the filter 40 is mounted to the floor 28 of the gas entrapment chamber 26 in a manner such that it is flush with or below the level of the floor. A countersunk bore may be provided in the floor 28 to enable such mounting. In so doing, the filter screen 52 extends directly to the floor of the gas entrapment chamber and avoids the formation of a step, caused by the skirt 56. Avoidance of a step is desirable in that such steps can give rise to regions of stagnation which, when the biological fluid contains blood, can result in the activation of clotting mechanisms.

The gas entrapment chamber is further characterized in that it is in fluid communication with the biological fluid outlet 20. The gas entrapment chamber is configured to have a large cross sectional area so that the velocity of fluid flowing therethrough will be greatly reduced relative to the remainder of the device. Such a reduction in velocity will enhance gas entrapment as it will allow gas entrained in the flow path to rise more easily against the slow downward direction of fluid flow. The use of the gas entrapment chamber 26 facilitates gas entrapment because a region of the chamber is above the bulk fluid flow path, and this provides a region in which gaseous emboli leaving the fluid may congregate.

The aspects of the invention described above relate primarily to the prevention of gaseous emboli formation and gas entrapment. That notwithstanding, the present invention is also configured to enhance heat exchange efficiency between the biological fluid and the heat exchanging medium. As noted above, heat exchange between the biological fluid and the heat exchanging medium occurs across the metal of the heat exchanger core 32. The corrugations 34 of the core 32 create a series of substantially parallel flow channels on the exterior and interior of the core. Biological fluid flowing through a channel on the exterior of the core will exchange heat with a heat exchanging medium flowing through channels on the interior of the core. The channels on the core interior form the walls that define the channels on the core exterior and vice versa. Although the flow of the biological fluid relative to the heat exchanging medium may be concurrent, counter-current flow is preferred. Likewise, heat transfer efficiency can be enhanced by causing the heat exchanging medium to become fully mixed.

Satisfactory mixing in the heat exchanging medium can be achieved by causing a jet-like flow through the inlet slot into the interior flow channels. Such a flow can be achieved by configuring the heat exchanging medium flow path in a manner such as is shown in FIG. 3a. FIG. 3a is a schematic representation showing a top view looking down on the lower portion 16 of the housing 12. As can be seen in FIG. 3a, the lower portion 16 of the housing includes a central wall 60 which will be positioned in the interior of the heat exchanger core (not shown) when the core is inserted into the housing. Flow diverters 62 and 64 extend from the edges of the central wall 60, extending into and substantially parallel with the interior of the heat exchanger core. The flow diverters 62, 64 and the interior corrugations of the heat exchanger core define the flow channels for the heat exchanging medium. Likewise, the central wall 60 and flow diverter 62 define a heat exchanging medium inlet chamber 66, while the central wall 60 and flow diverter 64 define a heat exchanging medium outlet chamber 68. The flow diverter 62 at the heat exchanging medium inlet chamber 66 includes an inlet slot 70 through which the inlet chamber 66 communicates with the interior flow channels of the heat exchanger core. Similarly, the flow diverter 64 at the heat exchanging medium outlet chamber 68 includes an outlet slot 72 through which the inlet chamber 68 communicates with the interior flow channels of the heat exchanger core. The outlet slot 72 is configured to be wider than the inlet slot 70. Fluid passing through the inlet slot will therefore have a higher velocity than fluid passing through the outlet slot. This increased velocity through the fluid inlet slot, referred to herein as jetting or jet-like flow, promotes enhanced mixing in the interior flow channels. This leads to a higher heat exchange efficiency. It is noted that the configuration of a narrow inlet slot and a wider outlet slot has been found to maximize heat transfer efficiency, since, if the slots are both narrow, the resulting reduction of heat exchange fluid traveling through the interior channels leads to a reduction in heat transfer efficiency. If the slots are both wide, the corresponding reduction in mixing leads to a reduction in heat transfer efficiency.

A schematic representation of the heat exchanging medium flow path is shown in FIG. 3b in which fluid can be seen traveling from the heat exchanging medium inlet chamber, through the inlet slot, along the interior flow channels of the heat exchanger, through the outlet slot and into the heat exchanging medium outlet chamber.

Figure 4:
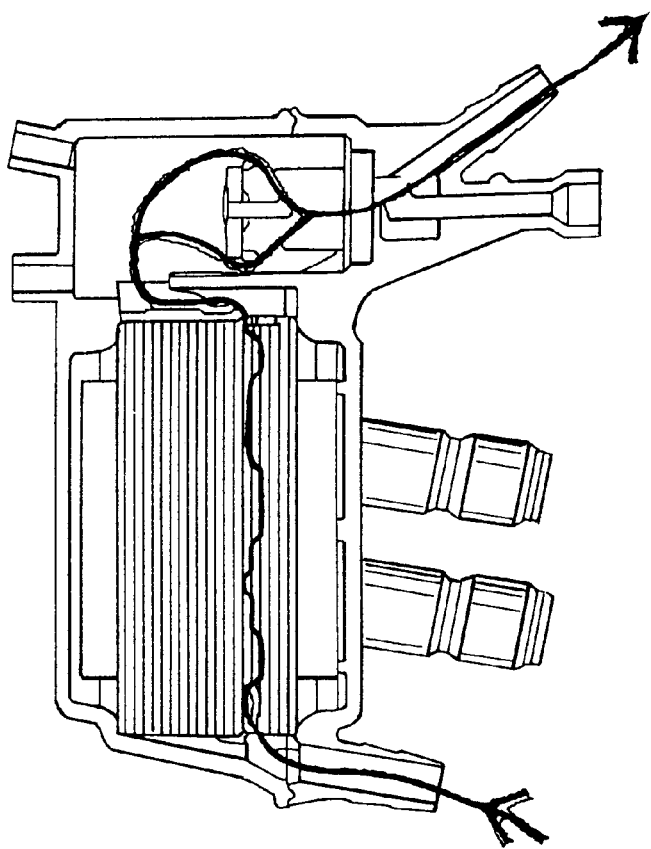
FIG. 4 is a schematic representation of a biological fluid flow path through one embodiment of the heat exchanger of the present invention.

For purposes of comparison, the flow path of the biological fluid is shown schematically in FIG. 4. In FIG. 4, the biological fluid is shown entering the biological fluid inlet, passing through the variable pitch manifold into the exterior flow channels defined by the heat exchanger core, traveling upward and over the biological fluid flow diverter wall into the gas entrapment chamber, and finally passing through the filter into the biological fluid outlet.

It is noted that in the present device, a first line can be defined by connecting a point at the center of the biological fluid inlet with a point at the center of the biological fluid outlet, and a second line can be defined by connecting a point at the center of the heat exchanging medium inlet with a point at the center of the heat exchanging medium outlet. In one preferred embodiment of the device, the first and second lines are not colinear. As such, the biological fluid inlet and outlet are said to be not colinear relative to the heat exchanging medium inlet and outlet. By being of a configuration that is not colinear, a more compact device results, because a configuration that is not colinear allows large connectors to be positioned at the respective inlets and outlets without interfering with one another. This is an improvement over devices in which the inlets and outlets are colinear, since space considerations, resulting from the use of large connectors, would otherwise necessitate the use of a device having a longer lineal length along the inlets and outlets.

As noted above, while the present device has use in many medical applications, it is particularly well-suited for use with cardioplegia apparatus. In that application, the biological fluid is a cardioplegia solution which has been defined above as a crystalloid solution, blood, or any combination of crystalloid solution and blood. The heat exchanging medium is preferably water.

The housing can be formed of any of a wide variety of polymeric materials known to be suitable for contact with blood or other biological fluids provided by or intended for a patient. It is preferred that the material comprising the housing be transparent to allow an operator using the device to inspect its interior either prior to or during use. Thus, in one preferred embodiment, the housing is formed of a plastic resin such as a clear polycarbonate. The filter preferably comprises a medical-grade polyester screen mounted on a USP Class 6 medical grade plastic frame. The material comprising the frame preferably does not include blockers of ultraviolet light, thereby allowing such UV light to be used to activate an adhesive used to secure the filter to the floor of the gas entrapment chamber. Suitable, medically acceptable adhesives are well-known in the art.

The heat exchanger core preferably comprises stainless steel, most preferably 304L or 316L stainless steel, although other metals suitable for medical use can be used as well. The metal optionally can be bright annealed.

In one embodiment, the surfaces of the device which contact the biological fluid may be coated with heparin or other coatings commonly used on surfaces coming into contact with biological fluids.

A potting material, such as polyurethane, is provided at each end of the heat exchanger core. Introduced in a fluid form, the potting material hardens in situ to provide a solid seal between the cuffs of the heat exchanger core and the respective portions of the housing. Likewise, the potting material seals the upper portion of the central wall and the flow diverters to the opposing housing portion, thereby preventing the heat exchanging medium from bypassing the interior flow channels and flowing directly from the heat exchanging medium inlet chamber to the heat exchanging medium outlet chamber.

Figure 5:
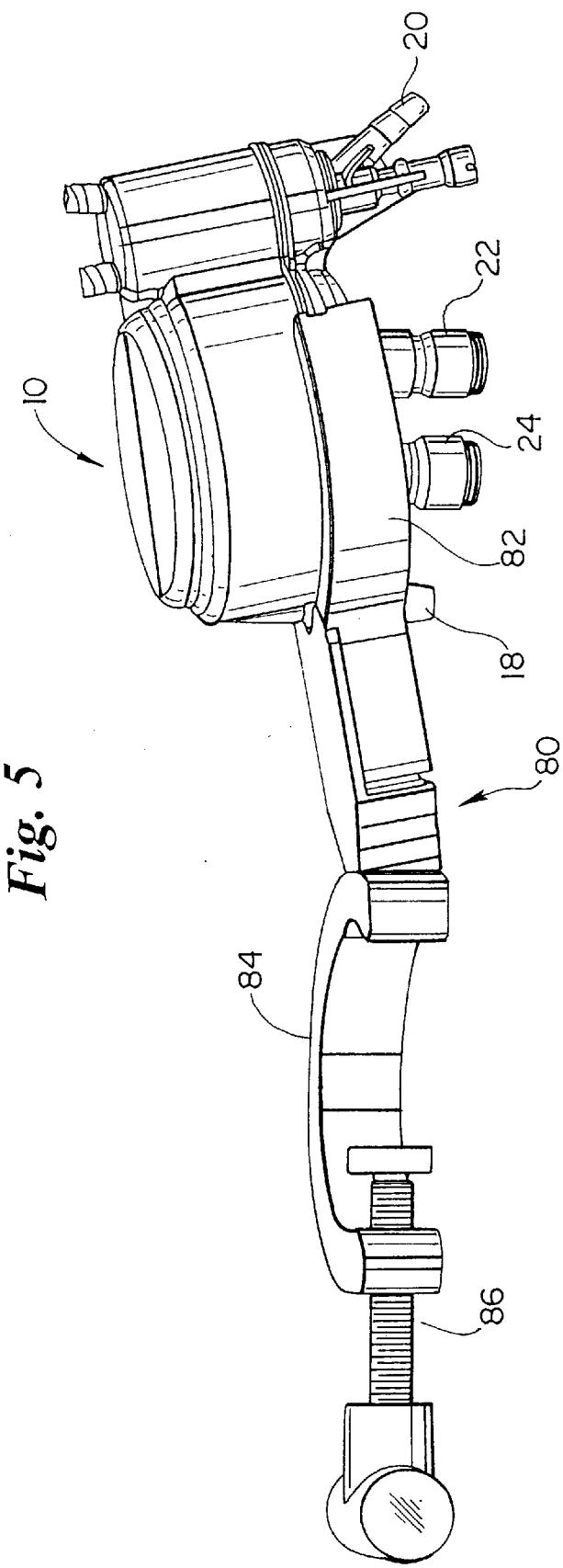
FIG. 5 is a representation of one embodiment of the heat exchanger of the present invention mounted in a holder.

As noted above, in one embodiment, the device is maintained in an orientation such that biological fluid in the biological fluid flow path is caused to travel upward toward the outlet at an angle of about 5° to about 20°, preferably 10°. One way in which the desired orientation can be achieved is through the use of a holder. As can be seen in FIG. 5, the device 10 is engaged by a holder 80. The holder includes a device engaging portion 82 and a clamping section 84 which may be adjusted by a screw 86 to mount the holder on a vertical pole or support (not shown). The engaging portion 82 of the holder extends from the clamping section at an angle which, when the holder is clamped to a vertical support, causes the engaging section to tip upward, away from the clamping section, at an angle of about 5° to about 20°, preferably 10°. Thus, when the device 10 is engaged with the holder, it is oriented such that biological fluid in the biological fluid flow path is caused to travel upward toward the outlet at an angle of about 5° to about 20°, preferably 10°. In the embodiment of the device 10 shown in FIG. 5, the biological fluid outlet 20 is raised above the biological fluid inlet 18. Additionally, each of the biological fluid inlet 18, the heat exchanging medium inlet 22, and the heat exchanging medium outlet 24, extends vertically downward from the device.

Figure 6:
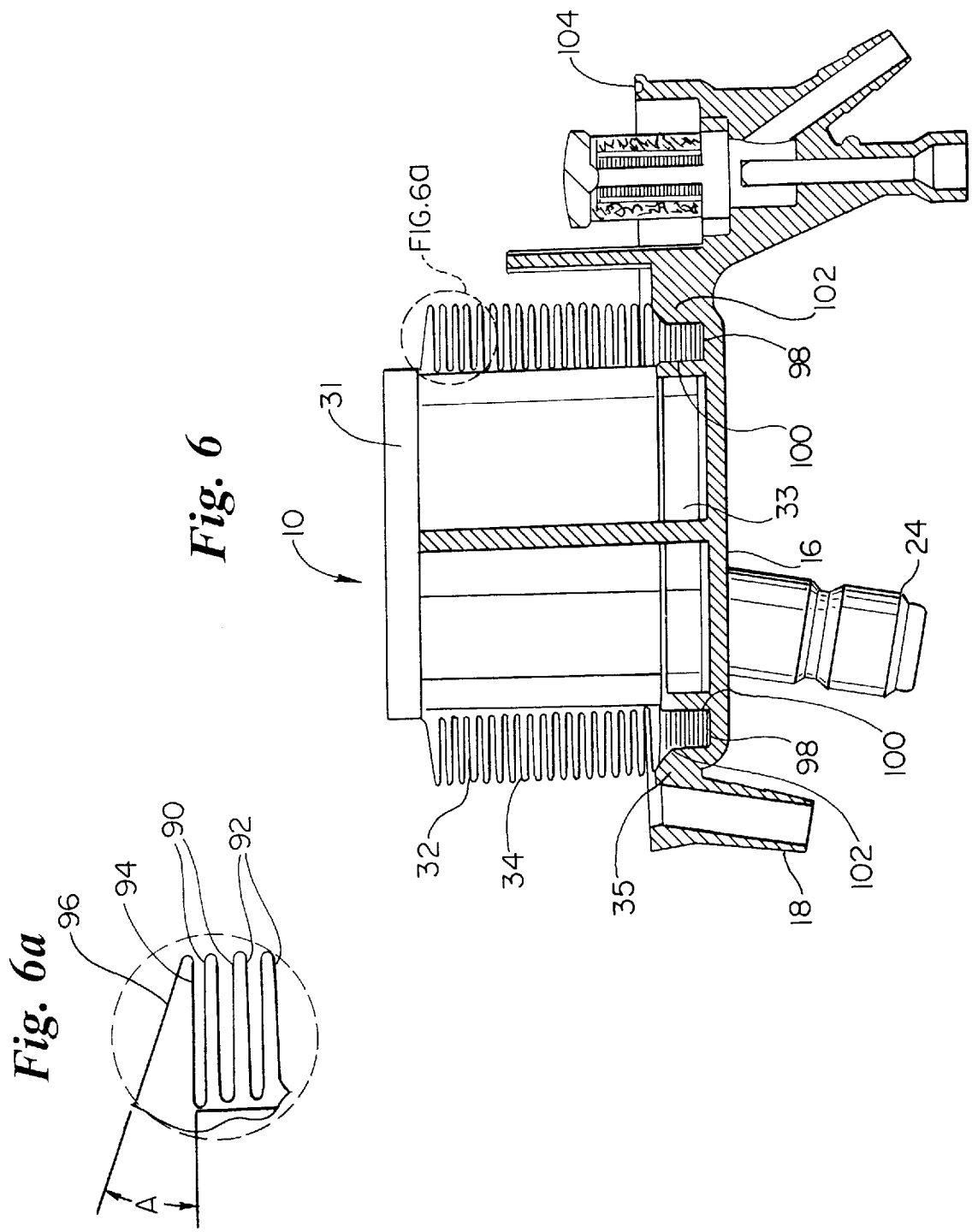
FIG. 6 is a schematic elevation of a section of a partially assembled heat exchanger of the present invention.

In a preferred embodiment core 32 is shaped to reduce the chance that air will be entrapped during the potting process and thus to improve the reliability of the manufacturing process of the heat exchanger. As best seen in FIGS. 6 and 6a, except for the corrugations at each end of the core, the corrugations comprise a first side surface 90 and a second substantially parallel side surface 92. The parallel side surfaces are oriented substantially normal to the axis of core 32. The corrugations at both ends of the core have an inner side surface 94 and an outer side surface 96. Inner side surface 94 is substantially normal to the axis of core 32. Outer side surface 96 is sloped at an angle A with respect to inner side surface 94. Angle A is preferably in the range of from about 3° to about 15°. Thus, outer surface 96 is positioned to have a positive slope between about 3° and 15° relative to a plane normal to the axis of the core formed by extending inner side surface 94. Although it is preferred that the outer side surfaces of the corrugations at both ends of the core be angled in this manner it may be desirable in some applications to slope only one of the outer side surfaces.

Figure 7:
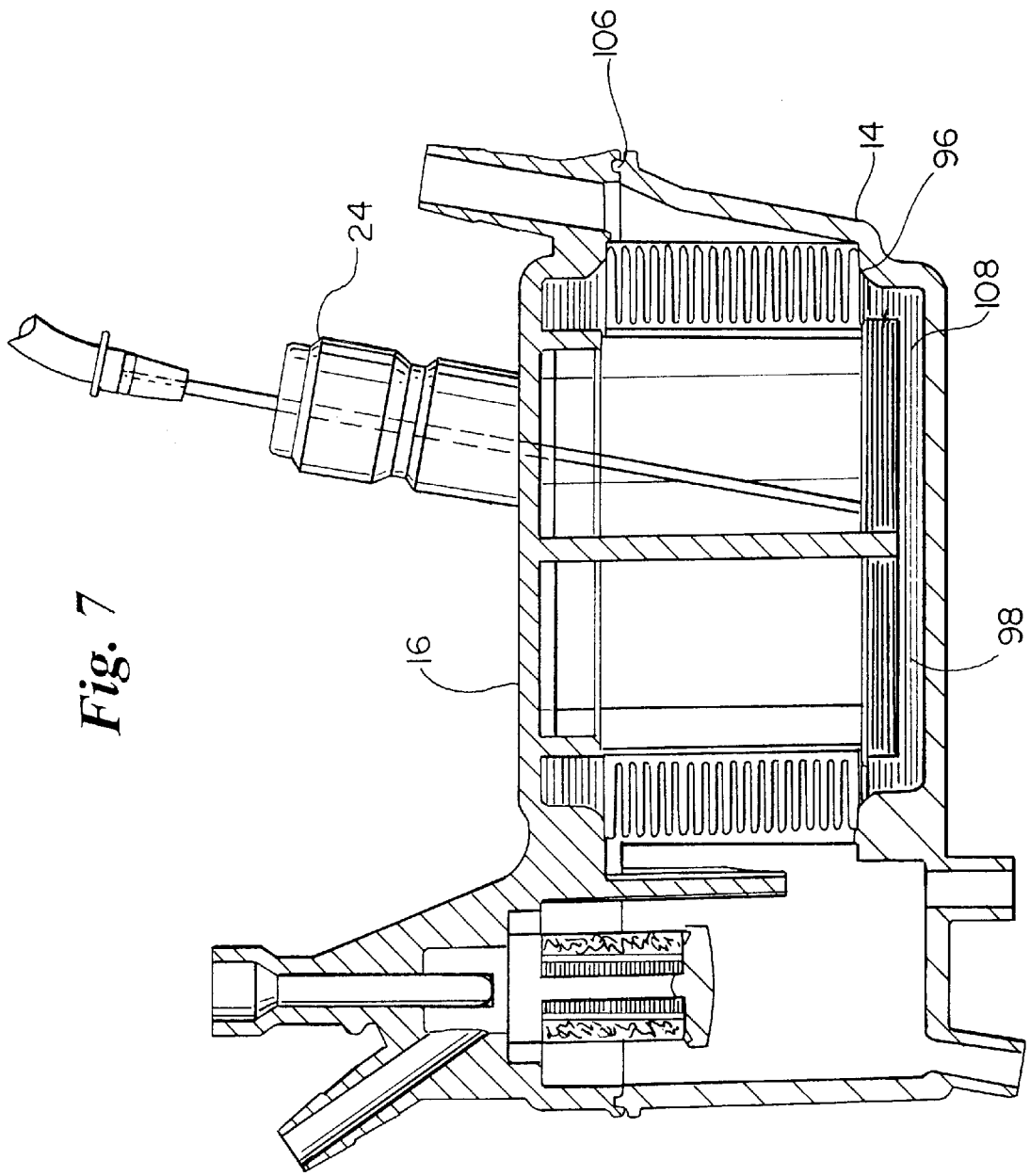
FIG. 7 is a schematic elevation of a section of a heat exchanger of the present invention during assembly.
Figure 8:
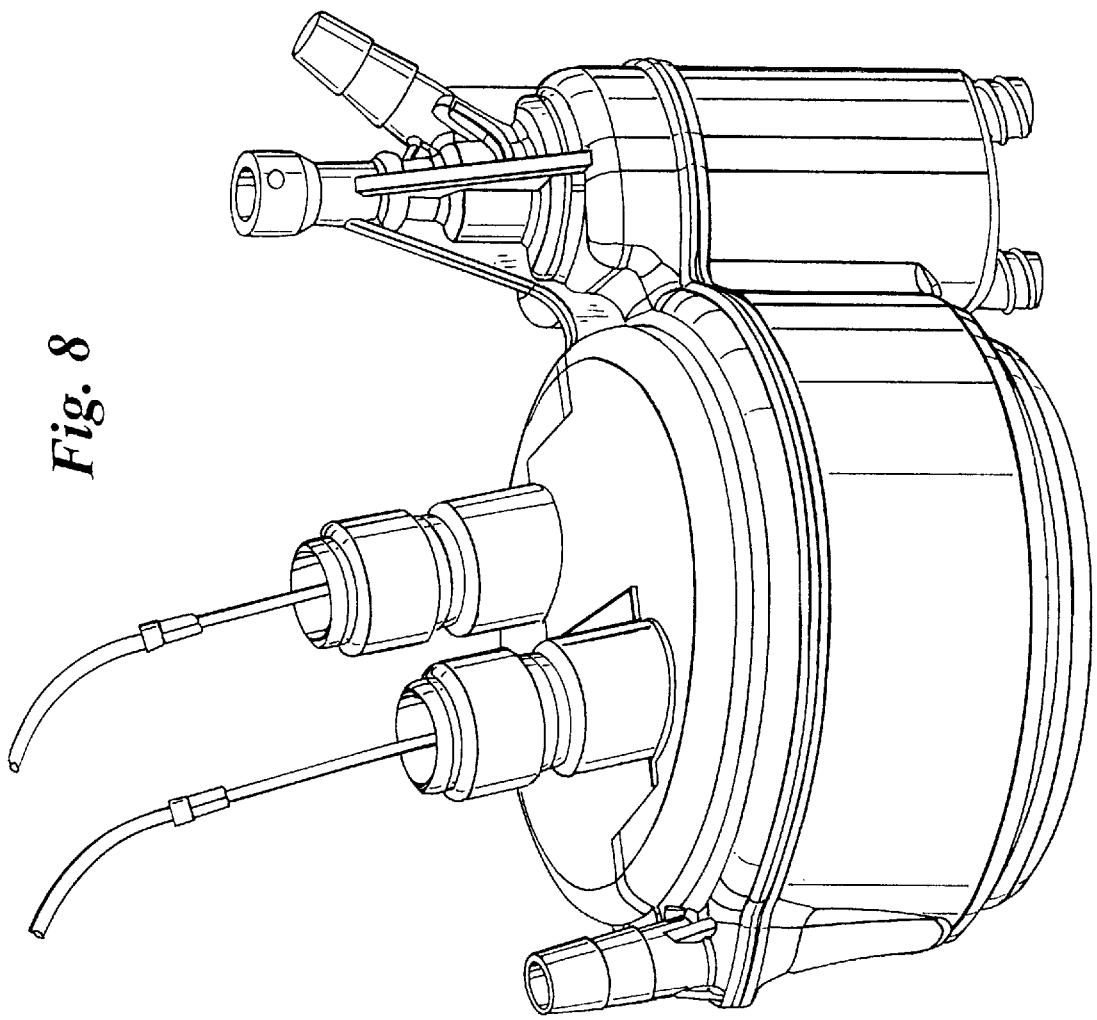
FIG. 8 is a perspective view of a heat exchanger of the present invention during assembly.

A heat exchanger with a core configured in this manner provides advantages during assembly of the device. FIGS. 6, 7 and 8 show the heat exchanger of the present invention during various stages of the assembly process. FIG. 6 is a sectional view of a partially assembled heat exchanger 10 before upper portion 14 has been added. At this stage of the assembly process a potting material 98 has been used to partially fill an annular trough in lower portion 16 formed between an inner annular ring 100 and an outer annular ring 102. After the potting material has been added the heat exchanger core 32 is inserted so that cuff 33 fits over inner annular ring 100 and into the annular trough. As core 32 is lowered into the annular trough outer side surface 96 is immersed in the potting material and comes to rest against shoulders 35 on the interior surface of lower portion 16. In this position substantially the entire surface of outer side surface 96 is in contact with the potting material 98. The positive slope of outer side surface 96 allows air to escape radially as core 32 is lowered into the annular trough and prevents or at least greatly reduces the chance that any air bubbles will be trapped between outer side surface 96 and potting material 98. This effect is enhanced by the spacing between the outer side surface 96 and lower portion 16 caused by standoffs 35. This constitutes a significant improvement over prior art medical heat exchangers with corrugated tubular cores having end corrugations with outer surfaces having no slope. Air is substantially more likely to be entrapped between the potting material and the outer side surface in these devices resulting in the devices being rejected for use.

The assembly in FIG. 6 is put into an oven to cure the urethane potting material in the lower portion. An adhesive such as a UV activated adhesive is placed in a groove 104 that surrounds lower portion 16. Upper section 14 is then added to the assembly by mating a tongue 106 located around the perimeter of upper portion 14 with groove 104. The assembly consisting of the upper portion mated with the lower portion is then clamped and put into a chamber where UV light is used to cure the UV adhesive. The urethane and UV adhesive curing steps are accomplished using methods, materials and equipment well known to those of skill in the art.

The heat exchanger is then inverted as shown in FIG. 7. A suitable potting material delivering means such as a hypodermic needle is inserted into heat exchange medium inlet 22 and heat exchange medium outlet 24 (as best seen in FIG. 8). Enough potting material is added to fill well 108 in upper portion 14. The potting material rises to a level so that substantially the entire surface of outer side surface 96 is in contact with potting material 98. Due to the positive slope of the outer surface 96 air does not become entrapped between the potting material 98 and the outer side surface 96 as the level of potting material rises. Instead, air and air bubbles are allowed to escape radially. The reduction of entrapped air is enhanced by standoffs (not shown) on the interior surface of upper portion 14 which spaces outer side surface 96 a distance 0.005" to 0.025" from the interior surface of upper portion 14 allowing air to be expelled as the level of potting material rises. After the appropriate amount of potting material has been added the potting material delivery means are removed and the heat exchanger is put back into the oven to cure the potting material.

Equivalents

Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A heat exchanger for use in medical applications which comprises:
    a) a housing formed of a biocompatible material and having a first end and a second end;
    b) a heat exchanger core which comprises a tube having a first end and a second end and a longitudinal axis, the core having a plurality of circumferential corrugations including first and second end corrugations adjacent the first and second ends of the core, respectively, to thereby define a plurality of exterior flow channels and interior flow channels, the first end corrugation having a first side surface adjacent the first end of the core, the second end corrugation having a first side surface adjacent the second end of the core;
    c) a first sealing member between the first end of the housing and the first side surface of the first end corrugation;
    d) a second sealing member between the second end of the housing and the first side surface of the second end corrugation, at least one of the first side surfaces of the first and second end corrugations being positioned at an acute angle relative to a plane normal to the axis of the core, the housing, core, and first and second sealing members defining:
        i) a biological fluid flow path across the exterior flow channels and in communication with a biological fluid inlet and a biological fluid outlet; and
        ii) a heat exchanging medium flow path across the interior flow channels and in communication with a heat exchanging medium inlet and a heat exchanging medium outlet, the biological fluid flow path and the heat exchanging medium flow path being isolated from one another.

2. The heat exchanger of claim 1 wherein both the first side surfaces of the first and second end corrugations are positioned at an acute angle relative to a plane normal to the longitudinal axis of the core.

3. The heat exchanger of claim 1 wherein the acute angle is between about 3° and 15°.

4. The heat exchanger of claim 2 wherein the acute angle is between about 3° and 15°.

5. The heat exchanger of claim 1 wherein the core is substantially cylindrical.

6. The heat exchanger of claim 2 wherein the core is substantially cylindrical.

7. The heat exchanger of claim 1 wherein each of the corrugations other than the first and second end corrugations have substantially opposing side surfaces which are positioned substantially parallel to a plane normal to the longitudinal axis of the core.

8. The heat exchanger of claim 2 wherein each of the corrugations other than the first and second end corrugations have substantially opposing side surfaces which are positioned substantially parallel to a plane normal to the longitudinal axis of the core.

* * * * *